United States Patent [19]
Paolo et al.

[11] Patent Number: 5,910,121
[45] Date of Patent: Jun. 8, 1999

[54] BIOPSY DEVICE

[75] Inventors: Avaltroni Paolo, Mantova; Casula Gianfranco, Milan, both of Italy

[73] Assignee: Gallini S.r.l., Mirandola, Italy

[21] Appl. No.: 09/002,500

[22] Filed: Jan. 2, 1998

[30]     Foreign Application Priority Data

Jan. 3, 1997  [IT]  Italy ................................ BO97A0001

[51] Int. Cl.$^6$ ................................................. A61B 10/00
[52] U.S. Cl. ......................... 600/562; 600/564; 600/567; 606/79; 606/167
[58] Field of Search ................................... 600/562, 564, 600/567; 604/79, 167, 181, 184, 185, 183

[56]           References Cited

U.S. PATENT DOCUMENTS

| | | | |
|---|---|---|---|
| 4,781,202 | 11/1988 | Janese ...................................... | 600/567 |
| 4,785,826 | 11/1988 | Ward ........................................ | 600/567 |
| 4,926,877 | 5/1990 | Bookwalter .............................. | 600/567 |
| 5,215,526 | 6/1993 | Deniega et al. ......................... | 604/164 |
| 5,357,974 | 10/1994 | Baldridge ................................. | 600/567 |
| 5,462,062 | 10/1995 | Rubinstein et al. ..................... | 600/567 |
| 5,573,008 | 11/1996 | Robinson et al. ....................... | 600/567 |
| 5,595,186 | 1/1997 | Rubinstein et al. ..................... | 600/564 |

*Primary Examiner*—Max Hindenburg
*Assistant Examiner*—Charles Marmor, II
*Attorney, Agent, or Firm*—Oblon, Spivak, McClelland, Maier & Neustadt, P.C.

[57]           ABSTRACT

A biopsy device includes a cylindrical outer cannula with a proximal end and a distal end, has a handle in the region of its proximal end and a cutting rim in the region of its distal end. An intermediate cannula, with a proximal end and a distal end, is disposed inside the outer cannula. The proximal end of the intermediate cannula is fixed to the proximal end of the outer cannula. The distal end of the intermediate cannula is provided with elastic resection means having their free ends bent inward, when they are in non-operation condition. An inner cannula, of smaller diameter, is slidably located inside the intermediate cannula. The inner cannula can be moved axially with respect to the intermediate and outer cannulas between an advanced position, in which said cannula pushes the resection means keeping their free ends open, and a retracted position, in which these resection means are released, and the free ends of the are bent elastically.

10 Claims, 2 Drawing Sheets

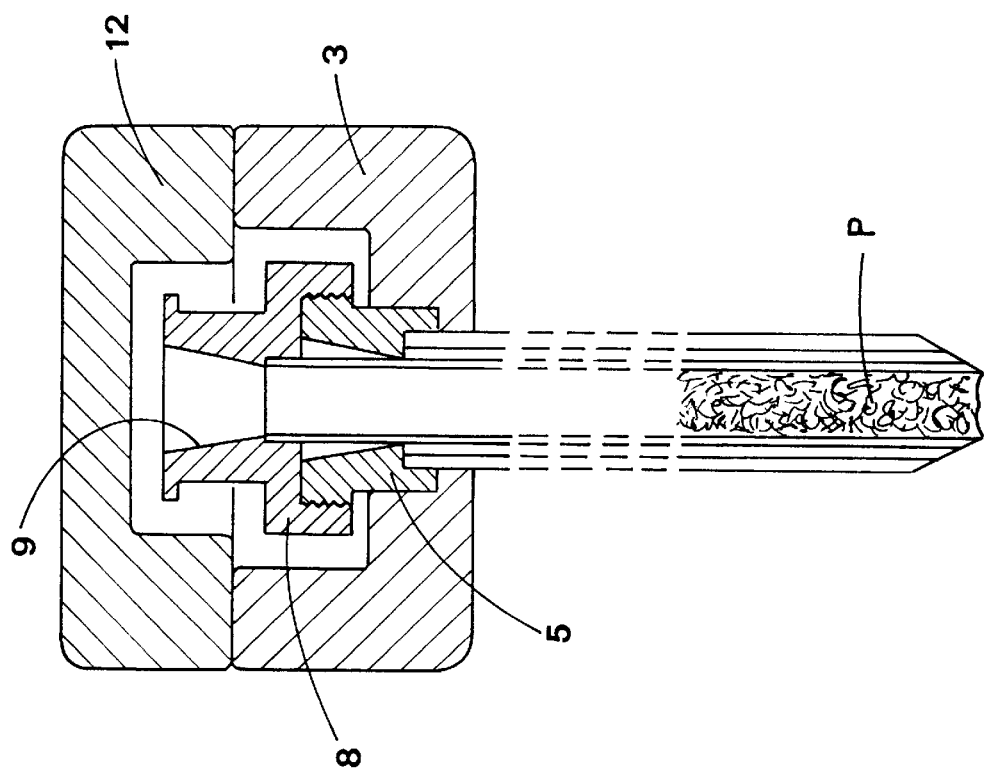
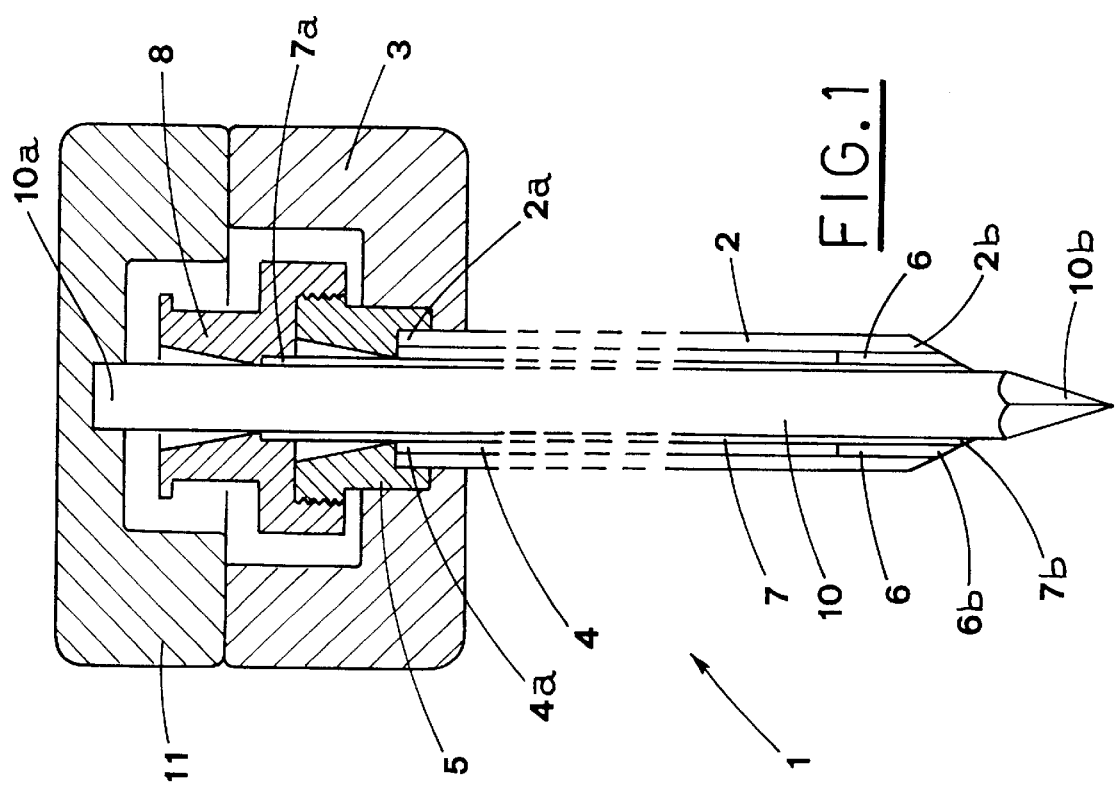

BIOPSY DEVICE

TECHNICAL FIELD

The present invention relates to surgical instruments for biopsy operations. In particular, the invention relates to a needle device for sampling bone and/or osteo-medullary tissues.

DESCRIPTION OF PRIOR ART

Different types of devices for biopsy, i.e. for removing small parts of tissue of humans and animals, usually for diagnosis, have been known for a long time.

In particular, rigid tissue, as e.g. bony and/or osteomedullary tissues, are traditionally taken by a cannula. Typically, the cannula has a handle made at a proximal end while another distal end is tapered and usually has a sharp edge.

A stylet with a suitably sharp distal end, can be slidably inserted inside the cannula.

The stylet is so long that the sharp end protrudes from the cannula, when the stylet is completely inserted therein.

The above described device is introduced through the skin up to a tissue to be sampled, in the beginning keeping the stylet inside the cannula.

This stylet facilitates the tissue perforation, even the most rigid outer part of a bone tissue, and prevents tissue other than the one to be sampled from introducing into the cannula. Then the stylet is withdrawn from the cannula and the cannula is pushed forward with a repeated rotatory movement, so as to cut a cylindrical portion of tissue.

Then, the cannula is further rotated and oscillated in order to separate a cylindrical sample.

Finally, the cannula is withdrawn from the tissue and the bioptic sample thus obtained is removed therefrom.

The most frequent disadvantage of these devices derives from the fact that it is difficult to separate the bioptic sample from the surrounding tissue. When this sample is not completely separated it is not fully extracted together with the cannula.

To overcome the problem, the cannula is imparted strong oscillations, that cause micro-fractures of the sample and surrounding tissue, thus increasing patient pains and slowing down the recovery.

Another disadvantage lies in fact that when the cannula is being removed, the sample can partially go out because only the tapered distal end of the cannula holds it.

Furthermore, the tapering, necessary for holding the sample, provoke a reduction of the dimension of the sample withdrawn by the device.

Moreover, because of the tapering, it is necessary to remove the bioptic sample from the cannula proximal end, making it pass along the whole cannula. This is usually done with the help of a suitable removal wire which is axially introduced into the cannula.

PRIOR ART REFERENCES

Various proposed devices have tried to overcome, at least partially, these disadvantages.

For example, U.S. Pat. No. 4,785,826 discloses a biopsy device formed by a first cannula and a second cannula set inside the first cannula. The first cannula has a tapered distal end, while the second cannula can slide axially.

Near its opening in which the tissue enters, the second cannula is provided with a flexible portion with sharp teeth.

Axial sliding of the second cannula makes the sharp teeth of the flexible portion bend against the inner surface of the first cannula tapered end. In this way, the flexible portion of the second cannula gets closed and holds the sample during extraction of the cannula.

According to the U.S. Pat. No. 5,333,619, a cylinder is introduced into the cannula. An approximately semi-cylindrical thin blade is fastened to a distal end of the cylinder so as to form a partial continuation of its shape.

The cylinder is introduced into the cannula until the blade penetrates between the cannula inner wall and a sample already received therein. The blade pushes the sample, also due to the tapering of the cannula distal end.

However, the above mentioned solutions have not been entirely satisfactory, because it is not very practical and because lacerations are still provoked in the tissue surrounding the bioptic sample.

The Italian Patent Application No. BO95A 000271 of the same Applicant, discloses a biopsy device including a cannula and a hollow cylinder. The cannula is tapered in the region of a distal end, and the hollow cylinder is introduced into the cannula.

At its distal end, the hollow cylinder is provided with a pair of opposite lobes, that have sharp ends aimed at partially going out of the cannula to cut the terminal part of the bioptic sample.

SUMMARY OF THE INVENTION

The object of the present invention is to provide a needle operated device, which allows tissue sampling ensuring that the bioptic sample is completely removed.

A further object of the invention is to propose a device that removes completely the bioptic sample without use of additional means and without any need of movements which could provoke further pains to the patient.

Another object of the present invention is to provide a biopsy device which obtains a relatively big sample, that is proportional to the device dimensions.

Yet a further object of the invention is to provide a biopsy device which allows easy removal of the bioptic sample from its distal end.

The above mentioned objects are obtained in a biopsy device including:

- a cylindrical outer cannula with a proximal end and a distal end, with a cutting rim made in said distal end;
- a handle fixed to said outer cannula proximal end;
- an intermediate cannula coaxially disposed inside said outer cannula, said intermediate cannula having a proximal end and a distal end, said intermediate cannula and outer cannula being joined to each other in the region of said outer cannula proximal end and intermediate cannula proximal end;
- an inner cannula, of diameter smaller than said intermediate cannula, slidably located inside said intermediate cannula, said inner cannula having a proximal end and a distal end;
- inner cannula support means fixed to said inner cannula proximal end for supporting said inner cannula and provoking axial movement of said inner cannula with respect to said intermediate cannula and outer cannula, so that said inner cannula can be moved between an advanced position, in which it protrudes from said intermediate cannula, and a retracted position;
- elastic resection means associated to said intermediate cannula distal end, with at least one free end of said resection means being released and elastically bent inward when said inner cannula is in said retracted position, while said inner cannula pushes said resection means when at said advanced position, so that said resection means are kept open.

BRIEF DESCRIPTION OF THE DRAWINGS

The characteristics of the invention have been pointed out in the following, with a particular reference to the enclosed drawings, in which:

FIG. 1 shows a schematic longitudinal sectional view of the biopsy device, being the subject of the present invention;

FIG. 2 shows the same sectional view during a further operation step;

FIG. 3 shows a particular of the previously mentioned sectional view, during another operation step;

FIG. 4 shows an enlarged particular of the subject biopsy device, in the above mentioned longitudinal sectional view;

FIG. 5 shows a different embodiment of the above particular of the biopsy device;

FIG. 6 shows a lateral view of the above mentioned particular of the biopsy device;

FIG. 7 shows a sectional view taken along the line VII—VII of the FIG. 6.

DETAILED DESCRIPTION OF THE PREFERRED EMBODIMENT

With reference to the above mentioned figures, reference numeral 1 indicates a biopsy device, in particular for rigid tissue, made according the present invention.

The device 1 includes an outer cannula 2, substantially cylindrical, made of metallic material, open at its ends. A handle 3 is fixed to a proximal end 2a of the cannula 2 to make handling easier.

A distal end of the cannula 2 has a sharp edge for facilitating penetration into the tissue.

An intermediate cannula 4, made of metallic material and likewise cylindrical, is set inside the outer cannula 2.

A proximal end 4a of the intermediate cannula 4 is fixed to the proximal end 2a of the outer cannula 2 by means of a binding barrel-like element 5. The binding barrel-like element 5 is fastened to the handle 3.

A distal end of the intermediate cannula 4 is provided with elastic resection means, that comprise preferably a pair of thin plates 6, made of metallic, suitably elastic material, in particular spring-steel. The plates 6 are arranged diametrically opposite to each other.

In practice, the plates 6 are made of cylindrical, arc-shaped parts, that adhere to the inner surface of the outer cannula 2.

The plates 6 are joined to the intermediate cannula 4, in the region of their rear ends 6a, substantially forming a prolongation of the cannula 4.

At their free ends, the plates 6 have pointed extensions 6b with respective cutting edges. The pointed extensions 6b are bent in such a way as to close one against the other, when the device is a non-operation condition (see particularly FIGS. 6 and 7).

Obviously, the plates 6 and the cannula 4 can be made in a single piece.

An inner metallic cannula 7, of small diameter, is slidably located inserted into intermediate cannula 4.

The inner cannula 7 passes through the binding barrel-like element 5. A proximal end 7a of the cannula 7 is integral with a support hollow knob 8, connected to the barrel-like element 5.

A distal end 7b of the cannula 7 has a cutting rim, so as to define a perfectly conical point, that facilitates the penetration in the tissue.

The hollow knob 8 is screwed onto the barrel-like element 5. When the hollow knob 8 is screwed or unscrewed, an axial sliding is caused for the inner cannula 7 with respect to the cannulas 2 and 4, which are joined to each other and remain stationary.

More precisely, the cannula 7 moves axially between an advanced position and a retracted position. In the advanced position, the cannula 7 pushes the pointed extension 6b keeping them open in cylindrical configuration, as seen in FIGS. 1 and 2.

When the cannula 7 is in the retracted position, the pointed extensions 6b are released and closed due to material elastic reaction. In this way, the bioptic sample is resected and can be easily extracted (FIG. 4).

A stylet 10 can be inserted, in a substantially known way, through the needle device formed by the three coaxial cannulas 2,4,7. The stylet 10 is preferably made of metallic material, and is substantially cylindrical.

In order to make possible the stylet introduction, an axial cone-shaped hole 9 is made in the support hollow knob 8.

The distal end 10b of the stylet 10 is sharp, while the proximal end 10a of the stylet is fastened to a cap 11.

The length of the stylet 10 is such that its sharp distal end 10b protrudes from the group of the cannulas, when the stylet is completely inserted therein and when the cap 11 is brought to abut on the handle 3.

After the stylet 10 has been withdrawn, an auxiliary cap 12, substantially of the same shape as the cap 11 of the stylet 10, can be applied to the handle 3 in order to cover the support hollow knob 8.

DESCRIPTION OF THE DEVICE OPERATION

For operation of the device, the stylet 10 is first completely introduced into the group of the coaxial cannulas 2, 4 and 7, until the cap 11 strikes against the handle 3, as seen in FIG. 1.

Afterwards, the needle device is introduced through the skin of a patient, until the tissue to be sampled is reached.

The distal sharp end 10b of the stylet 10 and the cutting rims of the cannulas 2, 4 and 7, formed in the respective distal ends 2b, 4b and 7b, facilitate this operation. In particular, the cone shape thus obtained facilitates perforation of the first layer of bone tissue, usually harder.

Reduction of the reaction pressure on the handle means that bone trabecula has been penetrated.

In this situation the stylet 10 is withdrawn and, after having covered the handle 3 with the auxiliary cap 12, the penetration is completed. Meanwhile, the needle is rotated.

During this step, the cannula 7 receives a cylindrical portion P of tissue to be sampled, thus forming the bioptic sample (FIG. 2).

It is to be pointed out that this portion of tissue being taken is perfectly cylindrical due to the cylindrical shape of the cannulas, which are not tapered or narrowed.

This allows to considerably increase the dimension of the sample, in practice by about 50% with respect to the traditional devices, all of which are tapered in the mouth region.

At this point, the support hollow knob 8, supporting the inner cannula 7, is unscrewed so as to determine axial sliding of the inner cannula 7 up to the retracted position (FIG. 3).

The retraction of the inner cannula 7 releases the plates 6, which have been kept open by it in the advanced position.

In this way, the pointed extensions 6b of the plates 6, suitably pre-loaded by the material elastic reaction, close towards each other. The bioptic sample is in this way resected and remains closed inside the needle device (FIG. 4).

Then, the device is extracted from the patient and, after having removed the auxiliary cap 12, the support hollow knob 8 is screwed again, so as to make the inner cannula 7 slide in the opposite direction towards the advanced position.

In this way, the pointed extensions 6b of the plates 6 are again pushed outwards by the inner cannula 7 and are pressed thereby against the inner surface of the outer cannula 2, in a cylindrical configuration.

This allows to remove the sample from the needle device with the help of a withdrawing wire of known, not shown, type.

DESCRIPTION OF A SECOND EMBODIMENT

The two plates 6b already mentioned for the preferred embodiment can be substituted by one single plate 116b, as shown in FIG. 5 where the device is in a non-operation condition. In this case, the cannula 7 keeps open or releases the plate 116b in a way similar to the one described in relation to the embodiment with two plates 6b.

ADVANTAGES OF THE DEVICE

Due to the perfect cylindrical form of the needle device, the taken sample can be easily removed from the device distal end, contrary to what happens with the traditional devices. Therefore, the user avoids any danger of injuring himself during introduction of the above mentioned withdrawing wire.

The biopsy device according to the present invention, is capable of separating the bioptic sample from the surrounding tissue without any additional movement which causes further sufferings to the patient, in particular oscillation and similar other movements. This was one of the objects of the invention.

Moreover, the bioptic sample integrity is guaranteed, especially during the extraction steps.

The dimension of this sample is considerably bigger with respect to the samples taken with traditional devices, which is more convenient for analysis necessities.

Another advantage of the invention lies in the fact that the above mentioned results are obtained by a needle device which does not need additional means for its operation.

In the description, mainly the bone and/or osteomedullary tissue samples have been referred to, anyway, the subject device can be used for biopsy of other tissue, soft tissue included.

It is understood that the foregoing embodiments have been disclosed by way of example, and that other modifications may occur to those skilled in the art without departing from the scope and spirit of the appended claims.

What is claimed is:

1. A biopsy device including:
    a cylindrical outer cannula with a proximal end and a distal end;
    a cutting rim made at said outer cannula distal end for facilitating penetration into tissue;
    a handle fixed to said outer cannula proximal end;
    an intermediate cannula coaxially disposed inside said outer cannula, said intermediate cannula having a proximal end and a distal end, said intermediate cannula and said outer cannula being joined to each other in the region of said outer cannula proximal end and said intermediate cannula proximal end;
    elastic resection means for surgically removing a bioptic sample associated with said intermediate cannula distal end, having at least one distal free end;
    an inner cannula, of a diameter smaller than said intermediate cannula, slidably located inside said intermediate cannula to control the position of said resection means, said inner cannula having a proximal end and a distal end;
    and inner cannula support means for supporting said inner cannula and providing axial movement of said inner cannula with respect to said intermediate cannula and said outer cannula, fixed to said inner cannula proximal end, so that said inner cannula can be moved between an advanced position in which said inner cannula distal end protudes from said intermediate cannula distal end, and a retracted position in which said inner cannula distal end is withdrawn to a position proximal of said intermediate cannula distal end;
    wherein said at least one free end of said resection means is released and elastically bent inward to cut and capture a bioptic sample when said inner cannula is moved from said advanced position to said retracted position;
    and wherein said inner cannula pushes said resection means when at said advanced position so that said resection means are kept open in a cylindrical configuration in order to receive a bioptic sample.

2. A biopsy device, according to claim 1, wherein said resection means include at least one plate made of elastic material and comprising a cylindrical section designed to adhere to an inner surface of said intermediate cannula, thus forming substantially a prolongation of said intermediate cannula.

3. A biopsy device, according to claim 2, wherein said plate has a pointed extension with a respective cutting edge bent inward.

4. A biopsy device according to claim 1, wherein said resection means include a pair of plates made of elastic material, said plates being arranged diametrically opposite to each other.

5. A biopsy device according to claim 4, wherein said plates have pointed extensions which are bent in such a way as to close one towards the other, when said inner cannula is in said retracted position.

6. A biopsy device according to claim 1, wherein said outer cannula is cylindrical with circular section along its whole length.

7. A biopsy device according to claim 1, wherein said outer cannula and said intermediate cannula are joined with each other by means of a barrel-like binding element fastened to said outer cannula proximal end, to said intermediate cannula proximal end, and to said handle.

8. A biopsy device according to claim 1, wherein said support means include a support hollow knob joined to said inner cannula proximal end, and which is in a screw engagement with a barrel-like binding element which joins with each other said outer cannula proximal end and said intermediate cannula proximal end.

9. A biopsy device according to claim 1, wherein an auxiliary cap is joined to said handle for covering said support means of said inner cannula.

10. A biopsy device according to claim 1, wherein a stylet is inserted into said inner cannula through an axial hole made in said support means, with a proximal end of said stylet being fastened to a cap, while a distal end of said stylet is sharp and protrudes from said inner, intermediate and outer cannulas when it is completely inserted therein.

* * * * *

UNITED STATES PATENT AND TRADEMARK OFFICE
CERTIFICATE OF CORRECTION

PATENT NO. : 5,910,121
DATED : June 8, 1999
INVENTOR(S) : Paolo Avaltroni, et al.

It is certified that error appears in the above-identified patent and that said Letters Patent is hereby corrected as shown below:

On the title page, item [19] should be:

--Avaltroni et al.--

On the title page, item [75] should be:

--[75] Inventors: Paolo Avaltroni, Mantova; Gianfranco Casula, Milan, both of Italy--

Signed and Sealed this

Twenty-third Day of January, 2001

Attest:

Q. TODD DICKINSON

Attesting Officer

Commissioner of Patents and Trademarks